US010835665B2

(12) United States Patent
Beisser

(10) Patent No.: US 10,835,665 B2
(45) Date of Patent: Nov. 17, 2020

(54) MANUALLY OPENABLE CLAMPING HOLDER WITH SENSOR

(75) Inventor: Nicolas Beisser, Hanau (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1144 days.

(21) Appl. No.: 13/883,848

(22) PCT Filed: Nov. 8, 2011

(86) PCT No.: PCT/EP2011/069633
§ 371 (c)(1),
(2), (4) Date: Jul. 23, 2013

(87) PCT Pub. No.: WO2012/062744
PCT Pub. Date: May 18, 2012

(65) Prior Publication Data
US 2013/0306543 A1    Nov. 21, 2013

(30) Foreign Application Priority Data
Nov. 8, 2010   (DE) .................. 10 2010 043 574

(51) Int. Cl.
```
A61M 5/14      (2006.01)
B25B 5/16      (2006.01)
B25B 5/06      (2006.01)
B25B 5/04      (2006.01)
F16M 13/02     (2006.01)
```
(52) U.S. Cl.
CPC ........ A61M 5/1414 (2013.01); A61M 5/1418 (2013.01); B25B 5/04 (2013.01); B25B 5/06 (2013.01); B25B 5/163 (2013.01); F16M 13/022 (2013.01); A61M 2205/3306 (2013.01); A61M 2205/3317 (2013.01); Y10T 29/49771 (2015.01)

(58) Field of Classification Search
None
See application file for complete search history.

(56) References Cited

U.S. PATENT DOCUMENTS

| | | | | |
|---|---|---|---|---|
| 3,492,500 A | * | 1/1970 | Hay | H03K 3/013 326/31 |
| 4,378,014 A | * | 3/1983 | Elkow | A61M 5/1684 128/DIG. 13 |
| 4,718,896 A | * | 1/1988 | Arndt | A61M 5/1689 604/253 |
| 5,567,120 A | | 10/1996 | Hungerford et al. | |

(Continued)

FOREIGN PATENT DOCUMENTS

| | | | |
|---|---|---|---|
| CN | 200987797 Y | * 12/2007 | |
| DE | 4205360 A1 | * 8/1993 | ........... A61B 8/0858 |

(Continued)

*Primary Examiner* — Krishnan S Menon
*Assistant Examiner* — Brad Gordon
(74) *Attorney, Agent, or Firm* — Jacobson Holman PLLC

(57) ABSTRACT

A manually openable clamping holder for releasably fixing a single-use medical device to a medical treatment apparatus has a sensor for detecting the position of the clamping jaws of the clamping holder. With the clamping holder, the correct equipping of a medical treatment apparatus with the appropriate single-use device can be monitored economically and with simple operation.

9 Claims, 2 Drawing Sheets

(56) References Cited

U.S. PATENT DOCUMENTS

| | | | | |
|---|---|---|---|---|
| 5,764,159 | A * | 6/1998 | Neftel | A61M 5/172 340/3.43 |
| 5,823,519 | A * | 10/1998 | Tunkers | B25B 5/122 269/201 |
| 5,951,509 | A * | 9/1999 | Morris | A61M 1/3681 250/432 R |
| 6,112,622 | A | 9/2000 | Reiman | |
| 6,192,284 | B1 * | 2/2001 | Golden | B23Q 17/003 700/150 |
| 6,202,290 | B1 * | 3/2001 | Kewitz | B21D 39/046 29/508 |
| 7,311,025 | B1 * | 12/2007 | Wilson, Jr. | B25B 13/481 81/429 |
| 2005/0131331 | A1 * | 6/2005 | Kelly | A61M 1/34 604/4.01 |
| 2006/0081547 | A1 * | 4/2006 | Queen | B25B 21/00 211/70.6 |
| 2007/0296366 | A1 * | 12/2007 | Quaid | B25J 9/1638 318/568.16 |
| 2010/0065700 | A1 | 3/2010 | Poncon et al. | |
| 2010/0113891 | A1 * | 5/2010 | Barrett | A61B 5/14535 600/301 |
| 2010/0309468 | A1 * | 12/2010 | Flank | A61B 5/14546 356/326 |
| 2011/0137162 | A1 * | 6/2011 | Bruce | A61M 5/14546 600/432 |
| 2011/0306866 | A1 * | 12/2011 | Thys | A61M 1/3653 600/407 |
| 2012/0146275 | A1 | 6/2012 | Choi et al. | |
| 2013/0041341 | A1 * | 2/2013 | Pazik | A61M 39/10 604/414 |

FOREIGN PATENT DOCUMENTS

| | | | | |
|---|---|---|---|---|
| EP | | 0289165 A1 * | 11/1988 | G01F 23/14 |
| EP | | 2060364 | 5/2009 | |
| WO | WO-2008047872 A1 * | | 4/2008 | B25J 9/1676 |

\* cited by examiner

MANUALLY OPENABLE CLAMPING HOLDER WITH SENSOR

CROSS-REFERENCE TO RELATED APPLICATIONS

This is a national stage of PCT/EP11/069633 filed Nov. 8, 2011 and published in German, which has a priority of German no. 10 2010 043 574.0 filed Nov. 8, 2010, hereby incorporated by reference.

BACKGROUND OF THE INVENTION

1. Field of Invention

The invention relates to a manually openable clamping holder, and in particular to a manually openable clamping holder for releasably fixing a single-use device to a medical treatment apparatus.

2. Description of the Prior Art

Medical treatment apparatuses often have holders for the fixing of a single-use medical device to the medical treatment apparatus during treatment. Medical treatment apparatuses according to the present invention are in particular blood treatment apparatuses. Blood treatment apparatuses can be for example devices for adsorption therapy, dialysis devices, infusion devices or devices for plasmapheresis. In order to prepare the medical treatment apparatus for the treatment of a patient, it is essential that it is equipped with a single-use medical device which is correctly attached to the medical treatment apparatus and is discarded after the treatment. Such a single-use device can be, for example, an adsorber or a dialysis filter. A further example is an infusion bottle, which is also attached by means of a holder to an infusion machine. After administration of the infusion fluid, the empty infusion bottle is removed from the holder and subsequently disposed of.

Single-use medical devices can differ from each other in, among other characteristics, their thickness.

In the prior art, spring clamps with at least two clamping jaws are in widespread use as holders for fixing a single-use medical device to a medical treatment apparatus.

In all these cases, a precondition for the error-free treatment of a patient is that prior to the beginning of the treatment the single-use medical device has been fixed to the medical treatment apparatus by means of the holder, and thereby made available for the treatment.

It can occur that an incorrect single-use medical device is accidentally fixed in the holder of the medical treatment apparatus. Due to this an incorrect infusion fluid could for example be administered to a patient, or an incorrect dialysis filter, which is unsuitable for the chosen treatment, could be used, which can have serious negative consequences for the patient's health.

When performing medical treatment—in particular adsorption therapy, which will be used as an example in what follows, and by means of which endotoxins are removed from the patient's blood by an adsorber—it can occur that the adsorber is not inserted in the holder provided for it, or does not remain there throughout the duration of the treatment. Due to inattention, or for the sake of convenience, the operating staff sometimes neglect to fix the adsorber in the holder provided for it. In this case, the adsorber instead hangs from the blood tubes which connect it to the patient's extracorporeal blood circulation. To ensure that the treatment is effective and risk-free for the patient, however, it is essential that the adsorber is fixed during the treatment in the holder provided for it. This is because it can occur that the intended direction of blood flow during the adsorber therapy is not adhered to due to operating errors, or that the weight of the adsorber causes it to sever its connections to the blood tubes, allowing blood to leak. Both occurrences pose a serious risk to the health of the patient undergoing treatment.

It is therefore the problem of the present invention to provide an economical and easy-to-operate device and a method which support the operating staff of a medical treatment apparatus in equipping the medical treatment apparatus with single-use medical devices at the correct time and in the correct manner, in order thereby to reduce the potential for errors during treatment.

SUMMARY OF THE INVENTION

This problem is solved by a clamping holder and a method according to the subject-matters of the independent claims. Advantageous and/or alternative further developments of the invention may be derived from the dependent claims.

A clamping holder according to the invention and a system according to the invention can be employed in any medical treatment apparatus in which a single-use device is fixed in a clamping holder. Blood treatment devices and infusion machines are examples of such medical treatment apparatuses. Among blood treatment devices, devices for adsorber therapy and dialysis devices may in particular be mentioned. The definition of the term "dialysis device" used here includes all devices and machines for performing dialysis, such as for example hemodialysis machines or machines for automatic peritoneal dialysis.

With a clamping holder according to the invention, any single-use device that is intended for use with a medical treatment apparatus can be releasably fixed to the medical treatment apparatus. Examples of single-use devices are adsorbers, dialysis filters and infusion bottles.

A clamping holder according to the invention comprises coacting clamping jaws, which coact to hold a single-use device by clamping the single-use device between them. At least one of the clamping jaws is displaceable between a closed position of the clamping jaws and a fully opened position of the clamping jaws. In the closed position of the clamping jaws, the clamping jaws cannot be pressed further together. The at least one displaceable clamping jaw is displaced into the closed position of the clamping jaws by the action of a closing element. From the closed position of the clamping jaws, the at least one displaceable clamping jaw can be manually displaced against the action of the closing element into the fully opened position of the clamping jaws. In the fully opened position of the clamping jaws, the clamping jaws cannot be spread further apart.

A clamping holder according to the invention also comprises a sensor for detecting the position of the clamping jaws.

In a preferred embodiment of a clamping holder according to the invention, the sensor detects whether the clamping jaws are in the closed position of the clamping jaws or not in the closed position of the clamping jaws. With this embodiment of a clamping holder according to the invention it can thus be determined with certainty whether or not a single-use device is clamped in the clamping holder. If there is no single-use device in the clamping holder, all clamping jaws are in the closed position of the clamping jaws; on the other hand, the at least one displaceable clamping jaw is not
} in the closed position of the clamping jaws when a single-use device is clamped between the clamping jaws.

In a further preferred embodiment of a clamping holder according to the invention, the sensor detects the position of at least one clamping jaw in a zone between the closed position of the clamping jaws and a fully opened position of the clamping jaws. This embodiment of a clamping holder according to the invention enables, alongside the simple detection of whether or not a single-use device is clamped between the clamping jaws, also the detection of a dimension of the single-use device, such as the circumference or diameter of the single-use device. Then, from the detection of a dimension of the single-use device, it is possible for example in a system according to the invention to distinguish different single-use devices from each other or determine the fill level of a single-use device.

A system according to the invention has, in addition to a clamping holder according to the invention, an evaluation unit for evaluating the position of the clamping jaws detected by the sensor and for ascertaining a deviation of the detected position of the clamping jaws from a specified position of the clamping jaws.

In order to ascertain a deviation, the evaluation unit preferably carries out a comparison of the data on the position of the clamping jaws detected by the sensor and the data on a specified position of the clamping jaws.

If it is ascertained that there is a deviation of the detected position of the clamping jaws from a specified position of the clamping jaws, it can reasonably be assumed that the medical treatment apparatus has been equipped with an incorrect single-use device.

Indication is then given, preferably using means for optical, acoustic and/or haptic signaling, of a deviation of the detected position of the clamping jaws from a specified position of the clamping jaws which was ascertained by means of the comparison that was carried out.

In addition to ascertaining a deviation, the data on the position of the clamping jaws detected by the sensor can also be used in the evaluation unit to determine the fill level of a single-use device with flexible walls. To do this the data on the position of the clamping jaws detected by the sensor is used in order to determine the circumference, and hence the volume, of a fluid in the single-use device.

A method according to the invention for equipping a medical treatment apparatus with a single-use device for use with the medical treatment apparatus, wherein the medical treatment apparatus comprises a manually openable clamping holder, which comprises coacting clamping jaws, of which at least one clamping jaw is manually displaceable against the action of a closing element from a closed position of the clamping jaws into an opened position of the clamping jaws, and a sensor for detecting the position of the clamping jaws, comprises the following steps:

manually holding the clamping jaws of the clamping holder open, inserting the single-use device between the clamping jaws, releasing the clamping jaws, closure of the clamping jaws by the action of the closing element until the clamping jaws contact the single-use device, detection by means of the sensor of the position of the clamping jaws around the single-use device, transmission to an evaluation unit of data captured by the sensor relating to the position of the clamping jaws, comparison in the evaluation unit of the data on the detected position of the clamping jaws with data on a specified position of the clamping jaws and signaling a warning if there is a deviation of the data on the detected position of the clamping jaws from the data on the specified position of the clamping jaws.

Additionally, a method according to the invention preferably has the step of blocking and/or interrupting the carrying out of functions on the medical treatment apparatus if there is a deviation of the data on the detected position of the clamping jaws from the data on the specified position of the clamping jaws.

BRIEF DESCRIPTION OF THE DRAWINGS

The invention is explained in detail below with the aid of the drawings.

The drawings show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various chances and modifications within the spirit and scope of the invention will become apparent to those skilled in the art from this detailed description.

Figure 1:
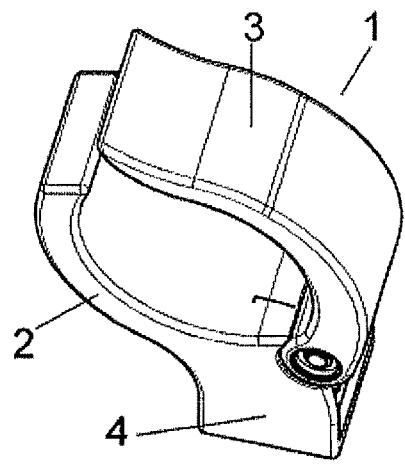
FIG. 1 a perspective view of a preferred embodiment of the invention.
Figure 2:
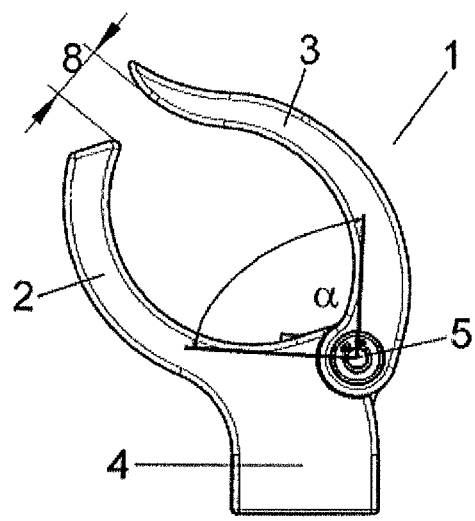
FIG. 2 a side view of the embodiment of the invention shown in FIG. 1.

The perspective view according to FIG. 1 shows a preferred embodiment of a clamping holder 1 according to the invention. The clamping holder 1 comprises a first clamping jaw 2 and a second clamping jaw 3. While the embodiment that is shown of a clamping holder 1 according to the invention comprises two clamping jaws 2, 3, further preferred embodiments of a clamping holder according to the invention can also comprise more than two clamping jaws. In the embodiment of a clamping holder according to the invention that is shown in the drawings, the first clamping jaw 2 is fixedly attached to a base part 4 of the clamping holder 1 and the second clamping jaw 3 is displaceable relative to the base part 4 around an axis of rotation 5 between a closed position of the clamping jaws and a fully opened position of the clamping jaws. While in the embodiment that is shown of a clamping holder 1 according to the invention only one of the clamping jaws is displaceable, in further preferred embodiments of a clamping holder according to the invention more than one clamping jaw, or even all clamping jaws, can be displaceable.

Figure 3:
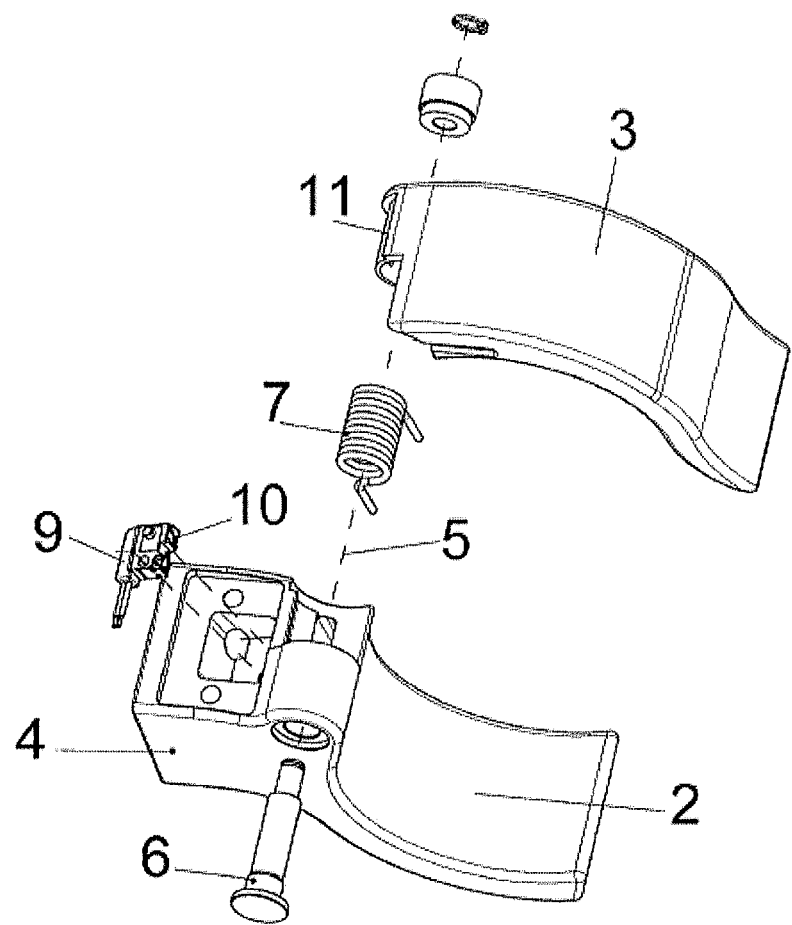
FIG. 3 an exploded view of the embodiment of the invention shown in FIG. 1.

As can be seen most clearly in the view shown in FIG. 3, the second clamping jaw 3 is rotatably disposed on the base part 4 by means of a bolt 6. The displaceable clamping jaw 3 is displaced by a closing element into the closed position of the clamping jaws. For this purpose the closing element has a helical torsion spring 7. Against the torsional moment applied by the helical torsion spring 7, and hence against the action of the closing element, the displaceable clamping jaw 3 can be displaced manually into an opened position of the clamping jaws by the application of a greater torsional moment in the opposite direction. This can be easily achieved if an operator holds one of the two clamping jaws 2, 3 in each hand and then moves the displaceable clamping jaw 3 around the axis of rotation 5 in a direction away from the first clamping jaw 2. The further apart the two clamping jaws 2, 3 are spread, the greater the angle α between the shoulders of the clamping jaws 2, 3 and the greater the distance 8 between the tips of the clamping jaws 2, 3. The maximum distance 8 and the greatest angle α is achieved when the clamping jaws 2, 3 are in the fully opened position of the clamping jaws. In the fully opened position of the clamping jaws, the clamping jaws 2, 3 cannot be spread further apart.

In place of a helical torsion spring, the closing element of the clamping holder 1 can also have other elements known from the prior art in order to achieve an effect of displacing one of the clamping jaws into the closed position of the clamping jaws.

The clamping holder 1 is preferably fixed by the end face of its base part 4 to a frame or housing component of a medical treatment apparatus. For this purpose the attachment means known from the prior art, such as for example screws, can be used. In order to obtain a greater distance between the clamping holder 1 and the medical treatment apparatus, an arm or support member can be disposed between the clamping holder 1 and the frame or housing component of the medical treatment apparatus. This is particularly advantageous for the attachment of single-use devices of which at least a portion has a large circumference, and which therefore must be disposed at a greater distance from the medical treatment apparatus.

The clamping holder 1 additionally has a sensor 9 for detecting the position of the clamping jaws 2, 3.

The sensor of a clamping holder according to the invention can be an optical, magnetic or electromechanical sensor. An example of an optical sensor is a photoelectric barrier, which can be realized by a light emitting diode or a laser diode and a phototransistor. Possible implementations of a photoelectric barrier used as an optical sensor are known to the skilled person from the prior art. As magnetic sensors, Reed relays and Hall sensors can be used. Feelers and potentiometers are examples of possible electromechanical sensors. Additional possible implementations of the sensor of a clamping holder according to the invention are known to the skilled person from the state of the art.

The sensor of a clamping holder according to the invention can be a switching sensor, by means of which two states can be differentiated. Thus a switching sensor can be used for example to detect whether the clamping jaws are in the closed position of the clamping jaws, and hence no single-use device is clamped in the clamping holder, or whether the clamping jaws are not in the closed position of the clamping jaws, because a single-use device is clamped in the clamping holder. Micro-switches are preferably used as switching sensors.

The sensor of a clamping holder according to the invention can also, however, be a non-switching sensor. Possible examples of these are potentiometers and inductive proximity sensors. Using non-switching sensors the exact positions of the clamping jaws can be detected. This permits for example the measurement of the angle α which is formed by the clamping jaws 2, 3. From the value of the measured angle α, it is possible for example to deduce the circumference or diameter of a single-use device clamped between the clamping jaws 2, 3. This in turn allows the type of single-use device to be deduced, and hence allows the equipping of a medical treatment apparatus with the correct single-use device to be monitored.

A clamping holder according to the invention can also have more than one sensor for detecting the position of the clamping jaws. Thus the position of each clamping jaw can be detected by a separate sensor. It is also possible that one of a plurality of sensors detects the position of a plurality of clamping jaws.

The sensor 9 in the embodiment shown in the drawings of a clamping holder according to the invention is a micro-switch. The micro-switch 9 has a displaceable pin 10, which is pushed in, against the action of a spring, by a raised area 11 on the displaceable clamping jaw 3 when the displaceable clamping jaw 3 is in the closed position of the clamping jaws. The pushing in of the pin 10 closes an electric circuit, and the sensor 9 detects the closed position of the clamping jaws.

With a clamping holder according to the invention it is thus possible economically and with simple operation to monitor the correct equipping of a medical treatment apparatus with the appropriate single-use medical device.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A manually openable clamping holder configured to releasably fix a single-use device to a medical treatment apparatus, the clamping holder comprising:
   coacting clamping jaws, of which at least one of the clamping jaws is displaceable manually against an action of a closing element from a closed position of the clamping jaws into an opened position of the clamping jaws, with the displaceable clamping jaw having a raised area thereon; and
   a micro-switch configured to detect the opened position of the clamping jaws as the clamping jaws fix the single-use device, with one of the clamping jaws having a base part that houses the micro-switch therein, and with the micro-switch having a displaceable pin that is displaced upon interaction thereof with the raised area of the displaceable clamping jaw, wherein the pushing of the pin closes an electric circuit such that the micro-switch detects the closed position of the clamping jaws.

2. The clamping holder according to claim 1, wherein the closing element has a helical torsion spring.

3. The clamping holder according to claim 1, wherein the single-use device is an adsorber, a dialysis filter, or an infusion bottle.

4. The clamping holder according to claim 1, wherein the single-use device is an infusion fluid container, or a dialysis filter.

5. A dialysis device comprising:
   a manually openable clamping holder configured to releasably fix a single-use device to the dialysis device, the clamping holder including
   coacting clamping jaws, of which at least one of the clamping jaws is displaceable manually against an action of a closing element from a closed position of the clamping jaws into an opened position of the clamping jaws, with the displaceable clamping jaw having a raised area thereon; and
   a micro-switch configured to detect the opened position of the clamping jaws as the clamping jaws fix the single-use device, with one of the clamping jaws having a base part that houses the micro-switch therein, and with the micro-switch having a displaceable pin that is displaced upon interaction thereof with the raised area of the displaceable clamping jaw, wherein the pushing of the pin closes an electric circuit such that the micro-switch detects the closed position of the clamping jaws.

6. A medical blood treatment device comprising:

a manually openable clamping holder configured to releasably fix a single-use device to the medical blood treatment device, the clamping holder including coacting clamping jaws, of which at least one of the clamping jaws is displaceable manually against an action of a closing element from a closed position of the clamping jaws into an opened position of the clamping jaws, with the displaceable clamping jaw having a raised area thereon; and a micro-switch configured to detect the opened position of the clamping jaws as the clamping jaws fix the single-use device, with one of the clamping jaws having a base part that houses the micro-switch therein, and with the micro-switch having a displaceable pin that is displaced upon interaction thereof with the raised area of the displaceable clamping jaw, wherein the pushing of the pin closes an electric circuit such that the micro-switch detects the closed position of the clamping jaws.

7. The medical blood treatment device according to claim 6, wherein the medical blood treatment device is a device for adsorption therapy, a device for an infusion of medical fluids, a device for dialysis, or a device for plasmapheresis.

8. A manually openable clamping holder configured to releasably fix a single-use device to a medical treatment apparatus, the clamping holder comprising:

coacting first and second clamping jaws, the second clamping jaw being displaceable and having a raised ridge area extending longitudinally across a portion thereof wherein said area is adjacent an axis about which the second clamping jaw rotates relative to the first clamping jaw, the second clamping jaw being displaceable manually against an action of a closing element from a closed position of the first and second clamping jaws into an opened position of the first and second clamping jaws; and a sensor configured to detect the first and second clamping jaws relative to each other as the first and second clamping jaws fix the single-use device, the sensor being a micro-switch having a displaceable pin that is pushed into the micro-switch upon interaction with the raised ridge area of the second clamping jaw so as to close an electric circuit such that the micro-switch detects the closed position of the first and second clamping jaws.

9. The clamping holder according to claim 8, wherein the displaceable pin is displaced by the raised ridge area when the second clamping jaw is in the closed position of the first and second clamping jaws.

* * * * *